United States Patent [19]

Hsu

[11] 4,203,862
[45] May 20, 1980

[54] LIQUID CRYSTAL COMPOSITION

[75] Inventor: Ying-Yen Hsu, Bridgewater, N.J.

[73] Assignee: Timex Corporation, Waterbury, Conn.

[21] Appl. No.: 972,556

[22] Filed: Dec. 22, 1978

[51] Int. Cl.$^2$ ............................ C09K 3/34; C02F 1/13
[52] U.S. Cl. ..................................... 252/299; 252/408;
[58] Field of Search ................. 252/299, 408; 350/350

[56] References Cited

U.S. PATENT DOCUMENTS

| | | | |
|---|---|---|---|
| 3,975,286 | 8/1976 | Oh | 252/299 |
| 4,000,084 | 12/1976 | Hsieh et al. | 252/299 |
| 4,043,935 | 8/1977 | Kanbe | 252/299 |
| 4,082,428 | 4/1978 | Hsu | 252/299 |
| 4,083,797 | 4/1978 | Oh | 252/299 |
| 4,096,086 | 6/1978 | Kanbe | 252/299 |
| 4,129,983 | 12/1978 | Yamazaki | 252/299 |
| 4,137,192 | 1/1979 | Matsufuji | 252/299 |
| 4,141,853 | 2/1979 | Hibino et al. | 252/299 |
| 4,143,947 | 3/1979 | Aftercut et al. | 252/299 |
| 4,147,651 | 4/1979 | Oh | 252/299 |

*Primary Examiner*—Teddy S. Gron
*Attorney, Agent, or Firm*—Edward J. Timmer

[57] ABSTRACT

The invention provides a nematic liquid crystal composition useful in electro-optical display devices, the composition comprising:
4-cyanophenyl-4'-butylbenzoate: 15–30 mole%
4-cyanophenyl-4'-heptylbenzoate: 20–40 mole%
4-pentylphenyl-4'-pentylbenzoate: 20–35 mole%
4-pentylphenyl-4'-(4''-pentylbenzoyloxy)-benzoate: 10–15 mole%
4-cyano-4'-pentylbiphenyl: 10–20 mole%
chiral additive: 0.05–0.8 mole%.

5 Claims, No Drawings

LIQUID CRYSTAL COMPOSITION

FIELD OF THE INVENTION

This invention relates to liquid crystal materials and, more particularly, to mixtures of liquid crystal materials to form a liquid crystal composition having particularly desirable properties.

DESCRIPTION OF THE PRIOR ART

As is now well known, various materials exhibit a mesophase over a temperature range adjacent their nominal melting point at which they behave neither as true liquids nor as crystalline solids. Such materials are referred to as liquid crystals, of which there are three classes. One of these classes is the nematic type in which the relatively long and thin molecules tend to line up parallel to each other in the mesophase. By their very nature liquid crystal materials exhibit both optical and electrical anisotropies. As to their dielectric properties, nematic liquids may be classified as exhibiting either negative dielectric anisotropy or positive dielectric anisotropy. The former type can be made to exhibit a dynamic scattering mode by the application of a suitable voltage across a thin layer of the material. On the other hand, in a positive dielectric anisotropy liquid crystal material, a suitable voltage causes the molecules to line up with the electric field so that optical devices utilizing such positive material are often referred to as field effect devices. Such positive dielectric anisotropic liquid crystal materials are especially desirable because of their relatively rapid response to turning on and off of the electric field and, if their positive dielectric anisotropy is quite large, their response to relatively low voltages. Thus, highly positive materials (in which the difference between the dielectric constant measured parallel to the axis of the molecule minus the dielectric constant measured perpendicular to this axis is quite large, i.e. on the order of 15 or more) are ideally suited for matrix type operation at relatively low switching voltages, and thus are especially suited for use in the ditigal display of a wrist watch, calculator and the like, where operation at low voltage is a valuable capability.

In addition to a high positive dielectric anisotropy, other desirable characteristics of a liquid crystal material include: a wide range of temperature (including room temperature, preferably at or near the midpoint of this range) at which the material is mesomorphic; high chemical stability as to, for example, moisture, heat, light (including ultraviolet as well as visible) and electric fields and relatively high transparency at least in the form of a thin layer, including preferably no spectrally selective absorption (i.e. the material is substantially colorless).

As evidenced in part in the following table, prior art workers have formulated many distinct types of liquid crystal materials and mixtures thereof in their attempts to satisfy all of the aforementioned characteristics. In the table, references 1-16 are particularly pertinent to the liquid crystal composition of the invention while the remainder may or may not be as pertinent.

TABLE OF REFERENCES

| U.S. PAT. NO. | INVENTOR | ISSUE DATE |
|---|---|---|
| 1. 3,915,883 | Van Meter et al | 10.28.75 |
| 2. 3,947,375 | Gray et al | 3.30.76 |
| 3. 4,001,137 | Steinstrasser | 1.4.77 |
| 4. 4,011,173 | Steinstrasser | 3.8.77 |
| 5. 4,046,708 | Dubois | 9.6.77 |
| 6. 4,048,089 | Arai et al | 9.13.77 |
| 7. 4,053,431 | Scherrer et al | 10.11.77 |
| 8. 4,058,478 | Boller et al | 11.15.77 |
| 9. 4,066,570 | Boller et al | 1.3.78 |
| 10. 4,069,167 | Inukai et al | 1.17.78 |
| 11. 4,073,742 | Erdman et al | 2.14.78 |
| 12. 4,076,646 | Nakamo et al | 2.28.78 |
| 13. 4,077,260 | Gray et al | 3.7.78 |
| 14. 4,077,900 | Pohl et al | 3.7.78 |
| 15. 4,083,797 | Oh | 4.11.78 |
| 16. 4,086,002 | Arora | 4.25.78 |
| 17. 3,826,757 | Wong | 7.30.74 |
| 18. 3,919,105 | Katagin et al | 11.11/75 |
| 19. 3,923,857 | Boller et al | 12.2.75 |
| 20. 3,925,444 | Boller et al | 12/9/75 |
| 21. 3,960,752 | Klanderman et al | 6/1/76 |
| 22. 3,963,311 | Boller et al | 6/15/76 |
| 23. 3,981,817 | Boller et al | 9/21/76 |
| 24. 3,984,344 | Cole | 10.5.76 |
| 25. 3,988,054 | Yaguchi et al | 10.26.76 |
| 26. 3,989,639 | Yaguchi et al | 11.2.76 |
| 27. 3,997,242 | Boller et al | 12.14.76 |
| 28. 4,000,084 | Hsieh et al | 12.28.76 |
| 29. 4,013,582 | Gavilovic | 3.22.77 |
| 30. 4,014,811 | Totani et al | 5.29.77 |
| 31. 4,017,416 | Inukai et al | 4.12.77 |
| 32. 4,020,002 | Oh | 4.26.77 |
| 33. 4,058,475 | Jinnai et al | 11.15.77 |
| 34. 4,061,587 | Scherrer et al | 12.6.77 |
| 35. 4,090,975 | Aldrich et al | 5.23.78 |
| 36. 4,113,647 | Coates et al | 9.12.78 |

SUMMARY OF THE INVENTION

According to the present invention, there is provided a mixture of nematic liquid crystal materials in prescribed proportions which exhibits all the desirable characteristics set forth above, namely, a high positive dielectic anisotropy, a wide mesomorphic temperature range, high chemical stability and high transparancy in thin layers. The liquid crystal composition of the invention comprises:

4-cyanophenyl-4'-butylbenzoate: 15–30 mole%
4-cyanophenyl-4'-heptylbenzoate: 20–40 mole%
4 pentylphenyl-4'-pentylbenzoate: 20–35 mole%
4-pentylphenyl-4'-(4''-pentylbenzoyloxy)benzoate: 10–15 mole%
4-cyano-4'-pentylbiphenyl: 10–20 mole%
with preferably a chiral additive selected from cholesteryl nonanoate and/or (+)-4-nitrophenyl-4'-(2-methylbutyl)-benzoate in 0.05–0.8 mole%.

DESCRIPTION OF THE PREFERRED EMBODIMENT

The liquid crystal composition of the invention is illustrated in greater detail by means of the following examples which are included for purposes of illustration rather than limitation.

EXAMPLE I 4-cyanophenyl-4'-butylbenzoate: 21.25 mole%
4-cyanophenyl-4'-heptylbenzoate: 27.71 mole%
4-pentylphenyl-4'-pentylbenzoate: 26.31 mole%
4-pentylphenyl-4'-(4''-pentylbenzoyloxy)-benzoate: 12.95 mole%
4-cyano-4'-pentylbiphenyl: 11.78 mole%
chiral additive (cholesteryl nonanoate): 0.1 mole%

The mixture of Example I exhibited a crystal-nematic temperature (CN) of −10° C. and a nematic-isotropic temperature (NI) of 62.5° C. To obtain data on the optical properties and operating characteristics of this mixture, the mixture was introduced into a watch display cell of the field-effect type of 10 micron average substrate spacing and the following electro-optic characteristics were measured at 25° C.:
Threshold Voltage: 1.5 v.
90% saturation voltage: 2.5 v.
Response Time (on): 150 ms
Response Time (off): 170 ms

EXAMPLE II 4-cyanophenyl-4'-butylbenzoate: 26.45 mole%
4-cyanophenyl-4'-heptylbenzoate: 30.69 mole%
4-pentylphenyl-4'pentylbenzoate: 21.83 mole%
4-pentylphenyl-4'-(4''-pentylbenzoyloxy)-benzoate: 10.72 mole%
4-cyano-4'-pentylbiphenyl: 10.31 mole%

The mixture of Example II exhibited a crystal-nematic temperature (CN) of −8° C. and a nematic-isotropic temperature (NI) of 59° C.

EXAMPLE III 4-cyanophenyl-4'-butylbenzoate: 15.16 mole%
4-cyanophenyl-4'-heptylbenzoate: 34.30 mole%
4-pentylphenyl-4'-pentylbenzoate: 20.23 mole%
4-pentylphenyl-4'-(4''-pentylbenzoyloxy -benzoate: 12.15 mole%
4-cyano-4'-pentylbiphenyl: 18.6 mole%

The mixture of Example III exhibited a crystal-nematic temperature (CN) of −10° C. and a nematic-isotropic temperature (NI) of 63.2° C.

EXAMPLE IV 4-cyanophenyl-4'-butylbenzoate: 21.37 mole%
4-cyanophenyl-4'-heptylbenzoate: 29.09 mole%
4-pentylphenyl-4'-pentylbenzoate: 22.97 mole%
4-pentylphenyl-4'-(4''-pentylbenzoyloxy)benzoate: 14.73 mole%
4-cyano-4'-pentylbiphenyl: 11.84 mole%

The mixture of Example IV exhibited a crystal-nematic temperature (CN) of −5° C. and a nematic-isotropic temperature (NI) of 67° C.

Generally, the mixtures were doped with chiral additive, cholesteryl nonanoate (0.05–0.15 mole%) or (+)-4-nitrophenyl-4'-(2-methylbutyl)-benzoate (0.3–0.5 mole%).

It is apparent from Examples I through IV that the liquid crystal compositions of the invention possess an advantageous combination of properties useful for electro-optical display applications. Not only do the compositions exhibit a wide mesomorphic temperature range, low threshold voltage, rapid response times, but they are also chemically stable against moisture, heat and ultraviolet or visible radiation. The appearance of the compositions in the test displays was substantially colorless.

The advantageous properties of the inventive liquid crystal compositions result from the specific components selected for the mixture as well as the concentration ranges employed and the interrelation of one material to the other. For example, the high positive dielectric anisotropy of the compositions is attributable to the presence of 4-cyano-4'-pentylbiphenyl, 4-cyanophenyl-4'-butylbenzoate and 4-cyanophenyl-4'-heptylbenzoate in the prescribed proportions whereas the chemical stability is attributable to the use of 4'-pentylphenyl-4'-pentylbenzoate, an alkylmonoester, and 4-pentylphenyl-4'-(4''-pentylbenzoyloxy) benzoate, an alkyldouble ester, as well as the aforementioned cyanoesters in the mixture. The colorless appearance of the composition is also attributable to the ester type materials in the mixture. Mixtures of the 4-cyano-4'-pentylbiphenyl compound with the aforementioned ester compounds in the prescribed concentration ranges provides a considerable nematic temperature range, typically from −10° C. to 67° C. The wide temperature range and relatively low melting point results from the combination of wide temperature range biphenyl and ester materials and the general eutectic effect of combining a plurality of at least analogous compounds which reduces the melting point of the mixture below even the lowest melting point of the components. The chiral additive is an optically active compound which acts like a cholesteric liquid crystal and assists in effecting the desired helical twist of the molecules in the display, thus tending to reduce the decay time and equalize the switch on and off times. Cholesteryl nonanoate is cholesteric in nature and exhibits a crystal-smectic temperature of 78° C., a smectic-cholesteric temperature of 79° C. and a cholesteric-liquid temperature of 90° C. This compound is described in the Oh patent, U.S. Pat. No. 3,975,286, as an additive to reduce decay time. (+)-4-nitrophenyl-4'-(2-methylbutyl)-benzoate exhibits a melting point at 63.7°–64.7° C. and is an optically active but not nematic liquid crystal. It acts like a chiral nematic when mixed with other liquid crystals, however. So long as the components of the inventive composition and their concentrations are maintained within the following ranges, superior properties will result:

4-cyanophenyl-4'-butylbenzoate: 15–30 mole%
4-cyanophenyl-4'-heptylbenzoate: 20–40 mole%
4-pentylphenyl-4'-pentylbenzoate: 20–35 mole%
4-pentylphenyl-4'-(4''-pentylbenzoyloxy)benzoate: 10–15 mole%
4-cyano-4'-pentylbiphenyl: 10–20 mole%
chiral additive: 0.05–0.8 mole%
preferably (cholesteryl nonanoate or (+)-4-nitrophenyl-4'-(2-methylbutyl)-benzoate)

Although response times vary somewhat depending upon the display cell spacing and alignment layer deposition angles (e.g. SiO deposition angle on the substrates), the turn-on response time is generally about 150 milliseconds and turn-off response time is generally about 170 milliseconds for compositions of the invention. Threshold and 90% saturation voltages are likewise slightly varied for different SiO deposition angles although generally they are on the order of 1.5 volts and 2.5 volts, respectively.

Generally, all of the ester type compounds of the above compositions may be easily made from readily available starting materials. Basically, the reaction is the well known one between an appropriately substituted phenol and the appropriately substituted acid chloride. For 4-cyanophenyl -4'-butylbenzoate and 4-cyanophenyl-4'-heptylbenzoate, synthesis procedures are set forth in more detail in the Boller et al patent, U.S. Pat. No. 4,058,478 issued Nov. 15, 1977. Procedures for 4-pentylphenyl-4'-pentylbenzoate and 4-pentylphenyl-4'-(4''-pentylbenzoyloxy) benzoate can be found in the Steinstrasser patent, U.S. Pat. No. 4,001,137 issued Jan. 4, 1977 and the Arora patent, U.S. Pat. No. 4,086,002 issued Apr. 25, 1978. Synthesis of 4-cyano-4'-pentylbiphenyl is found in the Gray patent, U.S. Pat. No. 3,947,375 issued Mar. 30, 1976.

While several embodiments of the invention have been disclosed herein, it will be appreciated that modification of these particular embodiments may be made without departing from the spirit and scope of the invention.

I claim:

1. A nematic liquid crystal composition comprising:
   4-cyanophenyl-4'-butylbenzoate: 15-30 mole%
   4-cyanophenyl-4'-heptylbenzoate: 20-40 mole%
   4-pentylphenyl-4'-pentylbenzoate: 20-35 mole%
   4-pentylphenyl-4'-(4''-pentylbenzoyloxy)benzoate: 10-15 mole%
   4-cyano-4'-pentylibiphenyl: 10-20 mole%

2. The composition of claim 1 including a chiral additive in the amount of 0.05-0.8 mole%

3. The composition of claim 2 wherein the chiral additive is cholesteryl nonanoate in an amount 0.05-0.15 mole%.

4. The composition of claim 2 wherein the chiral additive is (+)-4-nitrophenyl-4'-(2-methylbutyl)-benzoate in an amount of 0.3-0.5 mole%.

5. An electro-optical display including the nematic liquid crystal composition of claim 1.

* * * * *